(12) United States Patent
Tolbert

(10) Patent No.: US 6,523,354 B1
(45) Date of Patent: Feb. 25, 2003

(54) COOLING BLANKET

(76) Inventor: Deborah Ann Tolbert, 19419 Winthrop, Detroit, MI (US) 48235

( * ) Notice: Subject to any disclaimer, the term of this patent is extended or adjusted under 35 U.S.C. 154(b) by 0 days.

(21) Appl. No.: 10/094,177

(22) Filed: Mar. 8, 2002

(51) Int. Cl.[7] .............................................. F25B 21/02
(52) U.S. Cl. ............................ 62/3.5; 62/3.3; 62/259.3; 607/108; 607/114
(58) Field of Search ........................ 62/3.5, 3.3, 259.3; 607/108, 114

(56) References Cited

U.S. PATENT DOCUMENTS

| | | | | |
|---|---|---|---|---|
| 3,967,627 A | * | 7/1976 | Brown | 128/400 |
| 4,523,594 A | * | 6/1985 | Kuznetz | 128/402 |
| 4,777,802 A | * | 10/1988 | Feher | 62/3 |
| 4,859,250 A | * | 8/1989 | Buist | 136/225 |
| 5,097,829 A | * | 3/1992 | Quisenberry | 128/400 |
| 5,344,436 A | * | 9/1994 | Fontenot et al. | 607/104 |
| 5,653,741 A | * | 8/1997 | Grant | 607/114 |
| 5,860,292 A | * | 1/1999 | Augustine et al. | 62/269.3 |
| 6,062,210 A | * | 5/2000 | Welles | 126/208 |
| 6,354,099 B1 | * | 3/2002 | Bieberich | 62/259.3 |
| 2002/0026226 A1 | * | 2/2002 | Ein | 607/108 |
| 2002/0056281 A1 | * | 5/2002 | Bieberich | 62/259.3 |

* cited by examiner

Primary Examiner—William C. Doerrier
Assistant Examiner—Mark Shulman

(57) ABSTRACT

The present invention essentially comprises a cooling blanket having multiple pockets to contain a heat sink with the heat sink provided in the pocket, the heat sinks being either a thermoelectric cooling unit or a cold pack.

15 Claims, 4 Drawing Sheets

COOLING BLANKET

BACKGROUND OF THE INVENTION

1. Field of the Invention

The present invention relates to a cooling blanket for use in connection with a blanket. The cooling blanket has particular utility in connection with a cooling blanket to provide the user selective control of the temperature of the blanket.

2. Description of the Prior Art

Cooling blankets are desirable for providing a cool covering as during sleep to provide comfort. Cooling blankets are used on surgical patients that need their core temperature lowered, in the case of burns victims to cool the affected area, and to cool those suffering with a fever. Cooling blankets can also be used in the stead of air conditioning, and can be used to reduce night sweats. A need exists for a simple cooling blanket that does not require heat exchangers or support equipment.

The use of a blanket is known in the prior art. For example, U.S. Pat. No. 4,662,433 to Cahn et al discloses an individual comfort control device that has a blanket with internal ducts through which heat transfer foam is pumped to an external heat exchanger that is connected to the blanket ducts. However, the Cahn et al '433 blanket does not provide a blanket having individual pockets for placing heat sinks and does not provide a thermoelectric cooling unit as a heat sink.

Similarly, U.S. Pat. No. 4,132,262 to Wibell discloses a heating and cooling blanket that has heating elements for heating the blanket and cooling tubes that carry heat transfer fluid to an external heat exchanger. However, the Wibell '262 patent does not provide a blanket having individual pockets for placing heat sinks and does not provide a thermoelectric cooling unit as a heat sink.

Lastly, U.S. Pat. No. 4,527,566 to Abare discloses a body wrap that supports a hot or cold pack in close proximity to a wearer's anatomy. The Abare '566 patent does not disclose a blanket having individual pockets for placing heat sinks and does not provide a thermoelectric cooling unit as a heat sink.

While the above-described devices fulfill their respective, particular objectives and requirements, the aforementioned patents do not describe a cooling blanket that allows a cooling blanket to provide the user selective control of the temperature of the blanket. The Cahn et al '433, Wibell '262 and Abare '566 patents makes no provision for providing a blanket having individual pockets for placing heat sinks and does not provide a thermoelectric cooling unit as a heat sink.

Therefore, a need exists for a new and improved cooling blanket that can be used for a cooling blanket to provide the user selective control of the temperature of the blanket. In this regard, the present invention substantially fulfills this need. In this respect, the cooling blanket according to the present invention substantially departs from the conventional concepts and designs of the prior art, and in doing so provides an apparatus primarily developed for the purpose of a cooling blanket to provide the user selective control of the temperature of the blanket.

SUMMARY OF THE INVENTION

In view of the foregoing disadvantages inherent in the known types of a blanket now present in the prior art, the present invention provides an improved cooling blanket, and overcomes the above-mentioned disadvantages and drawbacks of the prior art. As such, the general purpose of the present invention, which will be described subsequently in greater detail, is to provide a new and improved cooling blanket and method which has all the advantages of the prior art mentioned heretofore and many novel features that result in a cooling blanket which is not anticipated, rendered obvious, suggested, or even implied by the prior art, either alone or in any combination thereof.

To attain this, the present invention essentially comprises a cooling blanket having multiple pockets to contain heat sinks with heat sinks provided in the pockets, the heat sinks being either a thermoelectric cooling unit or a cold pack.

There has thus been outlined, rather broadly, the more important features of the invention in order that the detailed description thereof that follows may be better understood and in order that the present contribution to the art may be better appreciated.

The invention may also include a temperature controller for the thermoelectric cooling unit, a power cord, a power source, an attachable edge and a power junction. There are, of course, additional features of the invention that will be described hereinafter and which will form the subject matter of the claims attached.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved cooling blanket that has all of the advantages of the prior art a blanket and none of the disadvantages.

It is another object of the present invention to provide a new and improved cooling blanket that may be easily and efficiently manufactured and marketed.

An even further object of the present invention is to provide a new and improved cooling blanket that has a low cost of manufacture with regard to both materials and labor, and which accordingly is then susceptible of low prices of sale to the consuming public, thereby making such cooling blanket economically available to the buying public.

Still another object of the present invention is to provide a new cooling blanket that provides in the apparatuses and methods of the prior art some of the advantages thereof, while simultaneously overcoming some of the disadvantages normally associated therewith.

Even still another object of the present invention is to provide a provide a cooling blanket that can be used instead of air conditioning.

Still yet another object of the present invention is to provide a cooling blanket that can be used to help reduce temperature due to fever.

Still even another object of the present invention is to provide a cooling blanket that can be used for reducing night sweats.

Yet still another object of the present invention is to provide a cooling blanket that can be used by hospitals to reduce core body temperature of patients requiring this procedure.

Even yet still another object of the present invention is to provide a cooling blanket that can be used to provide greater comfort for the user while sleeping.

Lastly, it is an object of the present invention to provide a cooling blanket that can be used for reducing hot flashes.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DESCRIPTION OF THE PREFERRED EMBODIMENT

Figure 1:
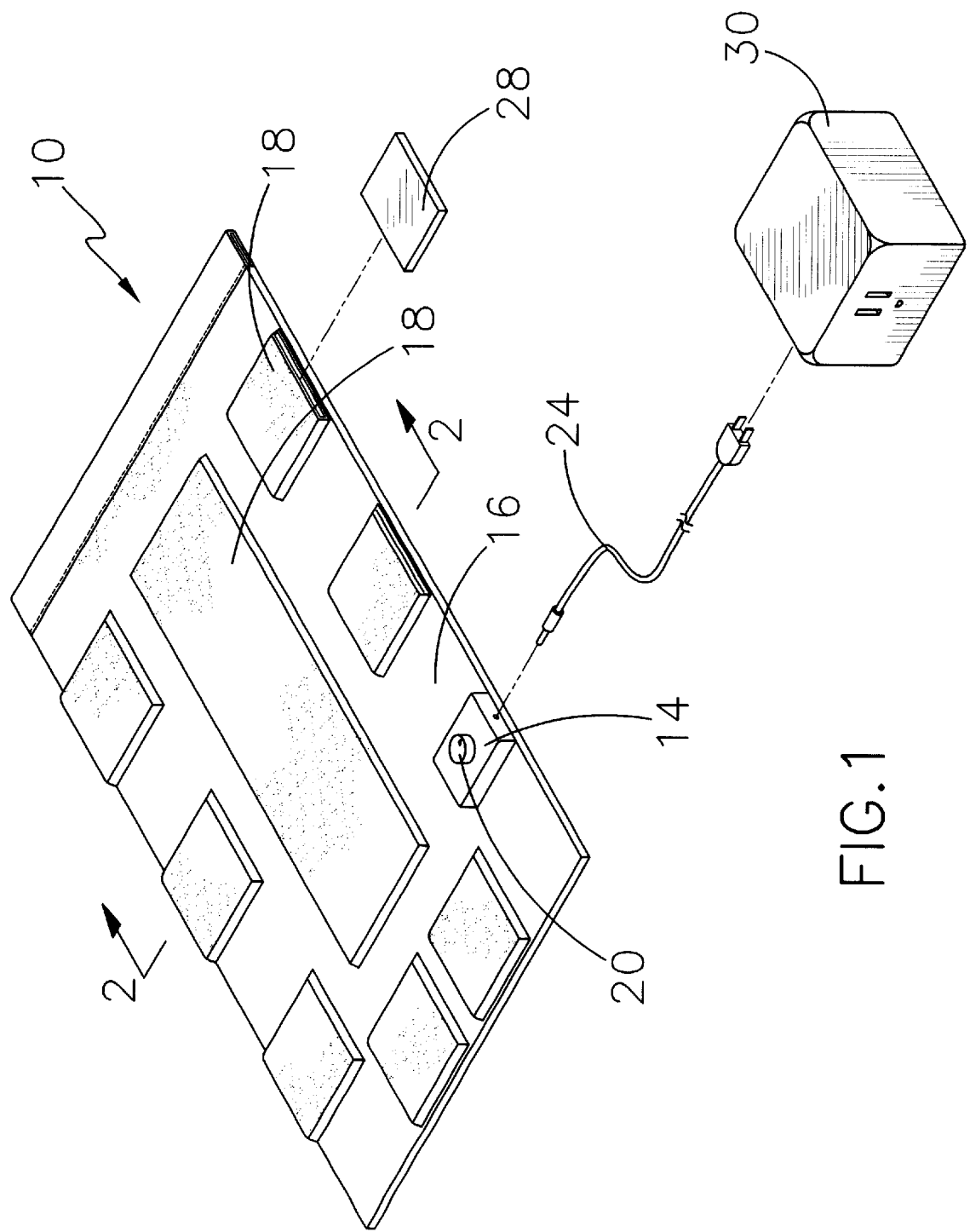
FIG. 1 is a front perspective view of the preferred embodiment of the cooling blanket constructed in accordance with the principles of the present invention.

Referring now to the drawings, and particularly to FIGS. 1–4, a preferred embodiment of the cooling blanket of the present invention is shown and generally designated by the reference numeral 10.

In FIG. 1, a new and improved cooling blanket 10 of the present invention for a cooling blanket to provide the user selective control of the temperature of the blanket. More particularly, the cooling blanket 10 has a thermoelectric cooling unit 12 heat sink electrically connected to a temperature control unit 14, for controlling the thermoelectric cooling unit 12. A blanket 16 has multiple individual pockets 18 for holding the thermoelectric cooling unit 12. A temperature control switch 20 is connected to the temperature control unit 14 for setting the temperature of the cooling blanket 10. An electrical power connection 24 electrically connects the temperature control unit 14 to an electrical power source 30. In a second embodiment the cooling blanket 10 would have thermal gel heat sinks 28 such as cold packs that would fit in the pockets 18 of the blanket 16.

Figure 2:
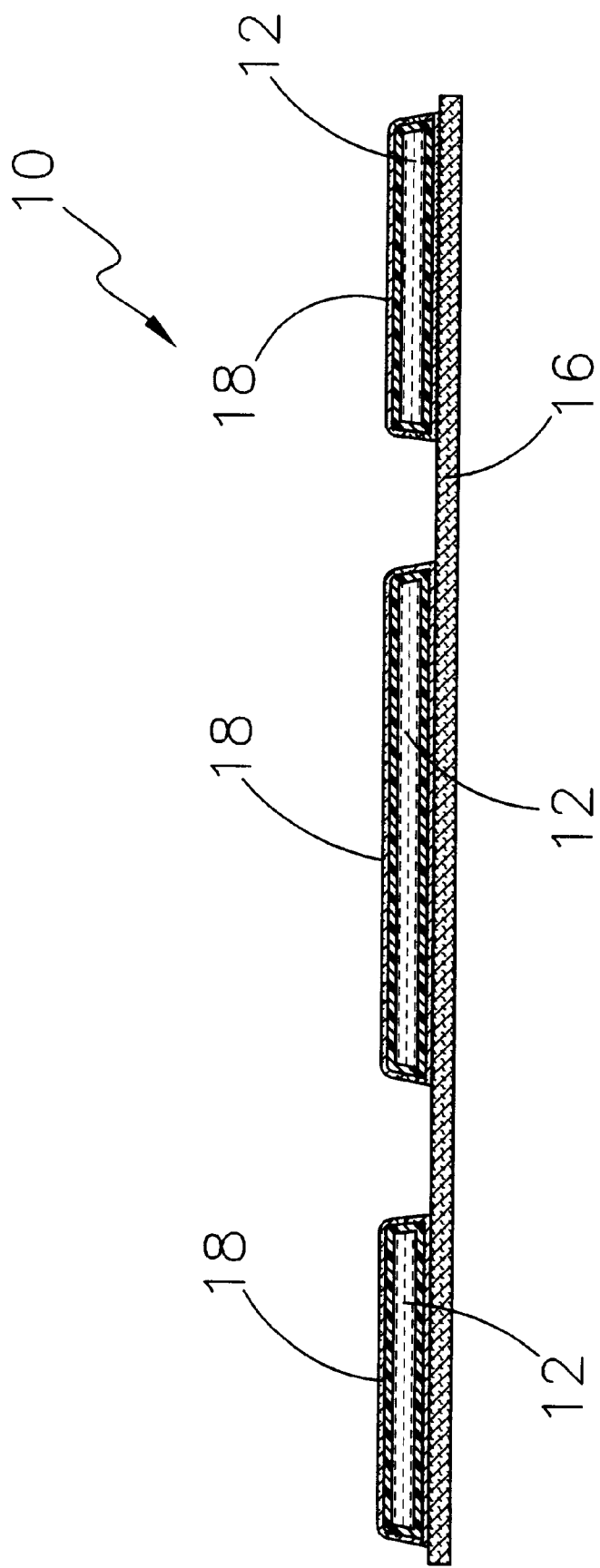
FIG. 2 is a section view 2—2 of FIG. 1 of the cooling blanket of the present invention.

In FIG. 2 the cooling blanket 10 is shown in section with the pockets 18 of the blanket 16 holding thermoelectric cooling unit heat sinks 12 or in a second embodiment holding thermal gel heat sinks 28 such as cold packs.

Figure 3:
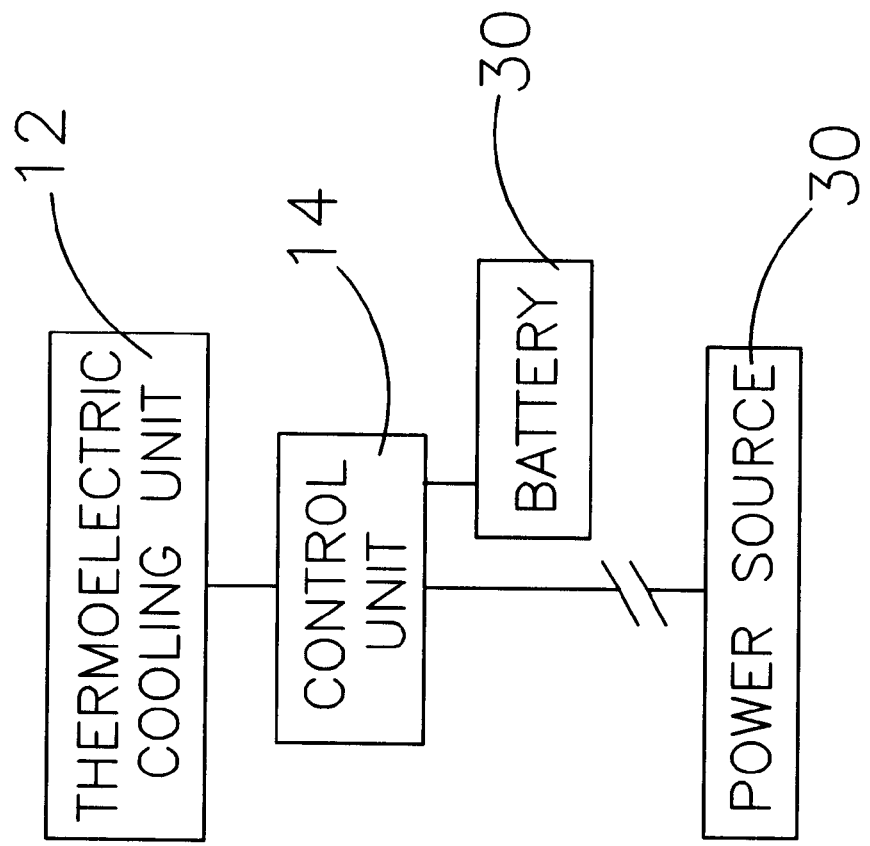
FIG. 3 is a block diagram view of the cooling blanket of the present invention.

In FIG. 3 a block diagram of the cooling blanket is shown with the thermoelectric cooling unit heat sink 12 connected to the temperature controller 14 that in turn is connected to an electrical power source 30.

Figure 4:
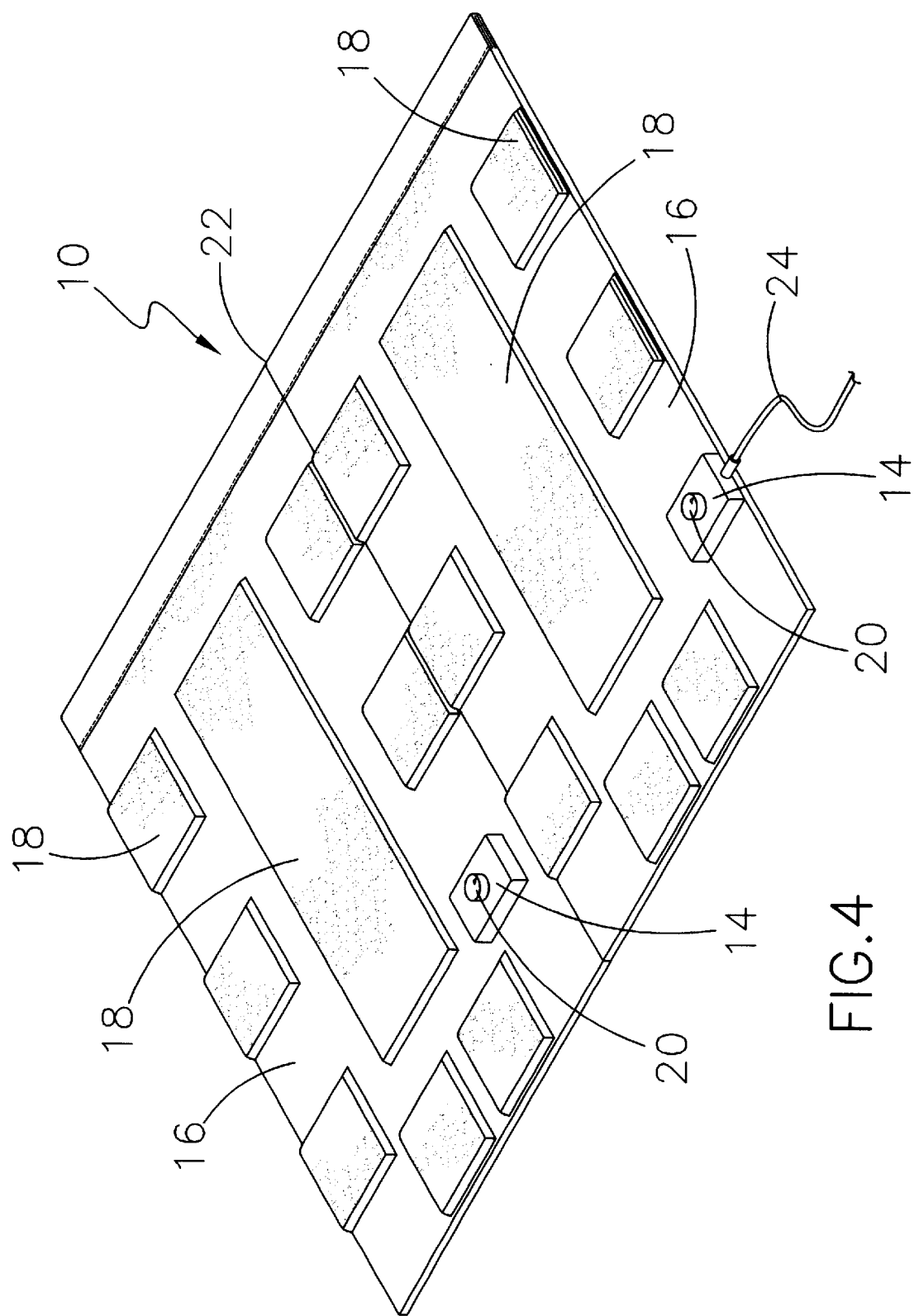
FIG. 4 is a front perspective view of two of the blankets connected at an edge of the cooling blanket of the present invention.

In FIG. 4 two of the cooling blankets are shown fastened along an edge. A fastener 22 is located along an edge of the blanket 16 for connecting to an edge of the blanket 16. An electrical jumper connection 26 (not shown) is electrically connected to the electrical power source 30 to allow additional cooling blankets to be electrically connected.

In use, it can now be understood that the temperature of the blanket is set with the temperature control switch 20 connected to the temperature control unit 14 for setting the temperature of the cooling blanket 10.

While a preferred embodiment of the cooling blanket has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, any color, shape or size, twin, full, queen or king blanket could be used. And although a cooling blanket to provide the user selective control of the temperature of the blanket has been described, it should be appreciated that the cooling blanket herein described is also suitable for use with cooling animals.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A cooling blanket comprising:
   a thermoelectric cooling unit;
   a thermally conductive water barrier encasing said heat sink; and
   a blanket having a plurality of pockets therein for holding said heat sink.

2. The cooling blanket of claim 1 further comprising:
   a fastener along an edge of said blanket for connecting to an edge of said blanket.

3. The cooling blanket of claim 1 further comprising:
   a temperature control unit, electrically connected to said thermoelectric cooling unit for controlling said thermoelectric cooling unit.

4. The cooling blanket of claim 1 further comprising:
   an electrical power connection electrically connecting said temperature control to an electrical power source.

5. The cooling blanket of claim 1 further comprising:

an electrical jumper connection electrically connected to said electrical power source to allow additional cooling blankets to be electrically connected.

6. A cooling blanket comprising:

a thermoelectric heat sink;

a thermally conductive water barrier encasing said thermoelectric heat sink; and a blanket having a plurality of pockets therein for holding said thermoelectric heat sink.

7. The cooling blanket of claim 6 further comprising:

a temperature control circuit, electrically connected to said thermoelectric cooling unit for controlling said thermoelectric cooling unit.

8. The cooling blanket of claim 6 further comprising:

a fastener along an edge of said blanket for connecting to an edge of said blanket.

9. The cooling blanket of claim 6 further comprising:

an electrical power connection electrically connecting said temperature control to an electrical power source.

10. The cooling blanket of claim 6 further comprising:

an electrical jumper connection electrically connected to said electrical power source to allow additional cooling blankets to be electrically connected.

11. A cooling blanket comprising:

a thermoelectric cooling unit;

a temperature control circuit, electrically connected to said thermoelectric cooling unit for controlling said thermoelectric cooling unit;

a thermally conductive water barrier encasing said thermoelectric cooling unit; and a blanket having a plurality of pockets therein for holding said thermoelectric cooling unit.

12. The cooling blanket of claim 11 further comprising:

a temperature control switch connected to said temperature control circuit for setting the temperature of said cooling blanket.

13. The cooling blanket of claim 11 further comprising:

a fastener along an edge of said blanket for connecting to an edge of said blanket.

14. The cooling blanket of claim 11 further comprising:

an electrical power connection electrically connecting said temperature control to an electrical power source.

15. The cooling blanket of claim 11 further comprising:

an electrical jumper connection electrically connected to said electrical power source to allow additional cooling blankets to be electrically connected.

\* \* \* \* \*